United States Patent [19]

Byrom

[11] Patent Number: 4,929,550
[45] Date of Patent: May 29, 1990

[54] PROCESS FOR THE PRODUCTION OF MICROBIAL CELLULOSE

[75] Inventor: David Byrom, Middlesbrough, England

[73] Assignee: Imperial Chemical Industries plc, London, England

[21] Appl. No.: 145,819

[22] Filed: Jan. 19, 1988

[30] Foreign Application Priority Data

Jan. 22, 1987 [GB] United Kingdom ............. 8701396

[51] Int. Cl.$^5$ .................... C12P 19/04; C12R 1/02
[52] U.S. Cl. ..................................... 435/101; 435/823
[58] Field of Search .............................. 435/101, 823

[56] References Cited

U.S. PATENT DOCUMENTS

| | | | |
|---|---|---|---|
| 4,209,590 | 6/1980 | MacFadden | 435/105 |
| 4,378,431 | 3/1983 | Brown | 435/101 |
| 4,745,058 | 5/1988 | Townsley | 435/101 |

FOREIGN PATENT DOCUMENTS

| | | | |
|---|---|---|---|
| 0228779 | 7/1987 | European Pat. Off. | 435/101 |
| 0260093 | 3/1988 | European Pat. Off. | 435/101 |
| 2265990 | 11/1987 | Japan | 435/101 |
| 2131701 | 6/1984 | United Kingdom . | |

OTHER PUBLICATIONS

Dudman, J. Gen. Microbiol., 22:25–39, (1960).
Steel et al., J. Gen. Microbiol., 17:12–18, (1957).
Schramm et al., J. Gen. Microbiol., 11:123–129, (1954).
Wright et al., Chem. & Ind., (Rev.), 74:18, (1955).
Shimwell, J. Inst. Brew., 62:338–343, (1956).
European Search Report re EP 88 30 0279.
Hestrin et al., "Synthesis of Cellulose by Acetobacter xylinium II. Preparation of Freeze-Dried Cells Capable of Polymerizing Glucose to Cellulose", Chemical Abstracts, vol. 49, No. 2, 25th Jan. 1955, No. 1143h.
Kang et al., "Microbial Technology. Microbial Processes," 2nd Ed., vol. 1, 1979, pp. 417–421, Chapter 13: pp. 419–420.
J. Levy et al., "Introductory Microbiology", 1973, pp. 95–113, part 4: "Bacteria and their Environment".

Primary Examiner—Herbert J. Lilling
Attorney, Agent, or Firm—Cushman, Darby & Cushman

[57] ABSTRACT

A process for the production of extra-cellular microbial cellulose having the following 4 steps: (a) a growth step in which a bacterium in cultured in stirred batch culture until the carbon source present is substantially exhausted, (b) an accumulation step in which the carbon source is supplied continuously to the culture, (c) a removal step and (d) a separation step. The microbial cellulose produced by the process is readily usable as a bulking agent in foods or as a tabletting aid.

7 Claims, 1 Drawing Sheet

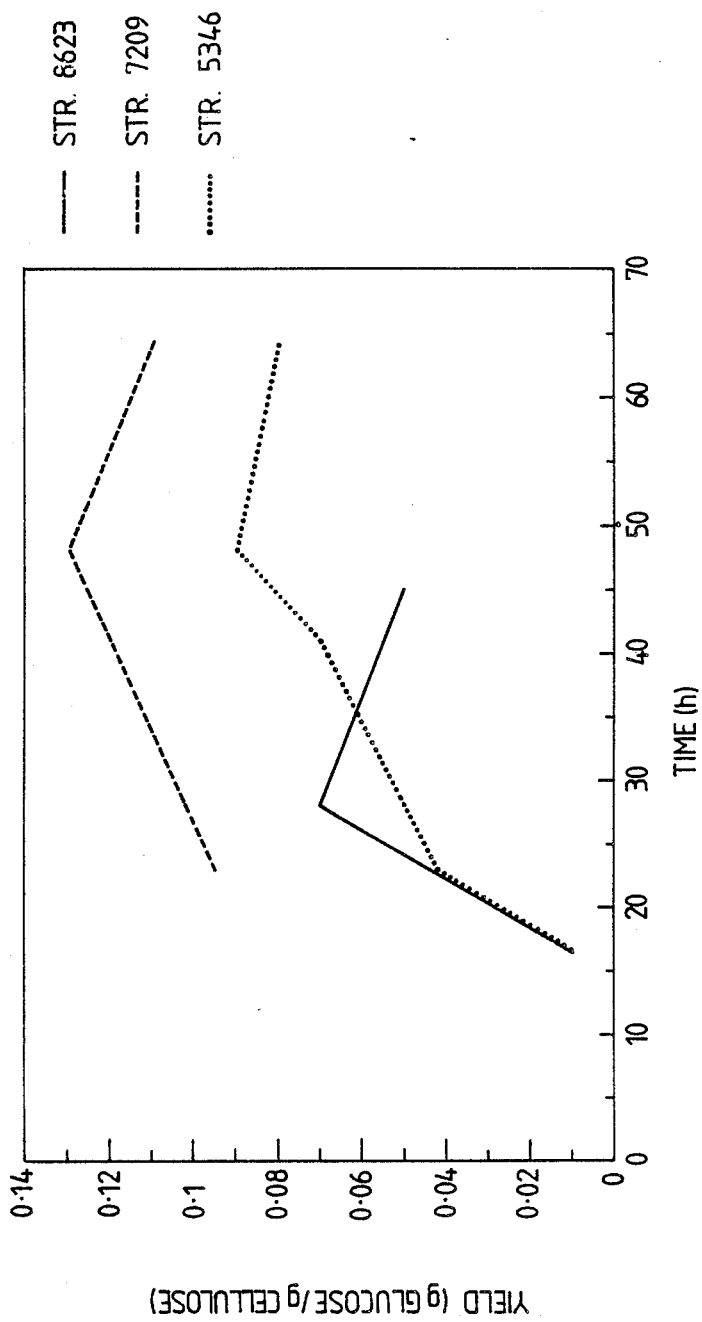

PROCESS FOR THE PRODUCTION OF MICROBIAL CELLULOSE

This invention relates to a process for the production of microbial cellulose.

A number of bacteria, particularly strains of the genus Acetobacter, can be cultivated to produce microbial cellulose. The microbial cellulose is produced extra-cellularly in the form of a fibril attached to the bacterial cell. Fibrils from different cells intermesh to give pellicles which are mixtures of cellulose and cells. A process for the production of microbial cellulose is disclosed in GB No. 2131701. To date processes for the production of microbial cellulose have used static cultivation methods with the pellicles of microbial cellulose being formed upon the surface of the static culture which is usually contained in shallow trays. Up to the present satisfactory yields of microbial cellulose have only been obtained by static cultivation. Attempts to make microbial cellulose reproducibly over periods of days by cultivation in shake flasks and stirred cultures have not been successful and have produced only low yields. Consequently it has to date been widely considered that static culture is necessary for a successful process for the production of microbial cellulose—see the articles by (a) Schramm & Hestin (J Gen Microbiol, 11, 123, 1954), (b) Wright & Walker (Chem & Ind (Rev), 74, 18, 1955), (c) Shimwell (J Inst Brew, 62, 339, 1956), (d) Steel & Walker (J Gen Microbiol, 17, 12, 1957a) and (e) Dudman (J Gen Microbiol, 22, 25–39, 1960).

Microbial cellulose pellicles have excellent liquid absorbing properties and can be used in a wide variety of medical applications, e.g. in absorbent pads as described in GB No. 2131701. For such medical applications the pellicles produced in static culture can be used directly. However, there are other non-medical uses for microbial cellulose and for such non-medical uses it is generally necessary for the pellicles to be broken into smaller pieces.

Microbial cellulose can be regarded as an extra-cellular polysaccharide. Such polysaccharides when produced by batch or continuous cultivation processes are normally produced with a substantial surplus of carbon source present in the medium under conditions of limitation by another nutrient such as the nitrogen or phosphorus sources. Often the carbon source is present in very considerable excess eg in processes for producing xanthan gums.

According to the present invention we provide a process for the production of extra-cellular microbial cellulose in which a bacterial strain capable of producing extra-cellular microbial cellulose is aerobically cultivated in a culture medium containing a carbon source and other necessary nutrients wherein the process comprises the steps:

(a) a growth step in which the bacterial strain is cultivated in stirred batch culture until substantially all the carbon source present has been utilized and the culture is carbon limited;

(b) an accumulation step in which the carbon source is supplied continuously to the carbon limited culture at a rate sufficient to maintain it in carbon limitation and to enable microbial cellulose to accumulate during stirred cultivation;

(c) a removal step in which bacterial cells and accumulated microbial cellulose are removed from the culture at the end of the accumulation step; and (d) a separation step in which microbial cellulose is separated from the cells.

Any bacterial strain capable of producing extra-cellular microbial cellulose may be used in the process of the invention. Suitable strains include strains belonging to the genus Acetobacter for instance strains of the species *Acetobacter xylinum,* such as strain ATCC 23769.

A very suitable strain is *Acetobacter orleanensis* strain NCIB 12584 received and accepted for deposit on Sept. 24, 1987, under the terms of the Budapest Treaty on the International Recognition of the deposit of microorganisms for the Purposes of Patent Procedure, by the National Collection of Industrial Bacteria, (NCIB) Torry Research Station, PO Box 31, 135 Abbey Road, Aberdeen, Scotland, UK, and variants and mutants derived from this strain. Another suitable strain is *Acetobacter aceti* subsp. orleanensis strain NCIB 8747 available from NCIB.

The growth and accumulation steps can be preferably carried out in the same fermenter. They can, however, be carried out in separate fermenters with the culture produced in the growth step being transferred from the fermenter in which it is produced into a second fermenter to which the carbon source is supplied continuously. This transfer can be made before the growth step is completed and before growth under carbon limitation has begun. The fermenters used can be stirred mechanically or can be of the "air-lift" type in which stirring is effected by blowing an oxygen-containing gas into the fermenter.

Examples of suitable "air-lift" fermenters are those described in our UK Patent Specifications Nos. 1353008, 1417486 and 1417487.

In the process of the invention the carbon source is auitably a carbon source for growth but this is not necessarily the case. A wide range of carbon sources may be used including lactate, ethanol, glycerol, molasses and other sugars such as fructose and particularly glucose. Suitably the culture medium for the growth step initially contains the carbon source at a concentration within the range 2 to 20 grm/l. During the accumulation step the carbon source is preferably supplied to the culture at a concentration within the range 1 to 10 grms/l per hour. A suitable culture medium for the growth and accumulation steps has the following composition:

| | |
|---|---|
| Peptone ('oxoid') | 5.0 g/l |
| Yeast extract ('oxoid') | 5.0 g/l |
| $Na_2HPO_4$ | 2.7 g/l |
| Citric acid | 1.15 g/l |
| Glucose | 20 g/l |
| Made up to pH 6.0 | |

The initial pH at which the growth and accumulation steps are carried out is suitably within the range 4 to 6.5 with a pH of approximately 5 being preferred. Suitably the growth and accumulation steps are carried out at a temperature within the range 15° C. to 35° C., preferably within the range 20° C. to 28° C.

During the accumulation step the culture is supplied with the carbon source at a rate such that the level of this source in the supernatant liquid is always in the range 0 to 0.5 g/l. Concentrations of other nutrients in the culture are gradually reduced until the supply of one or more of the other nutrients in the culture becomes exhausted. The accumulation step can be terminated at this point or further supplies of the other nutrients can be added. In the latter case cultivation can be continued until the culture becomes too viscous for satisfactory aeration. During the accumulation step extra-cellular microbial cellulose is formed as flocs rather than the large pellicles formed during static cultivation.

After completion of the accumulation step, the mass of cells and accumulated microbial cellulose is removed from the culture in the removal step by any suitable method. Preferably, this is done by filtration. The cellulose is thereafter separated from the cells in the separation step. The separation is suitably done by treating the mass of cellulose and cells with a reagent, eg an alkaline reagent, which will dissolve the cells without affecting the cellulose which can then be separated. A preferred method for dissolving the cells and separating the cellulose is to treat the cell/cellulose mass with a dilute sodium hydroxide solution, e.g. a 0.1–5.0% (preferably 0.3–3%) sodium hydroxide solution. After separation the microbial cellulose can be further treated, e.g. by drying.

The microbial cellulose produced by the process of the invention is more readily usable as a bulking agent in foods or as a tabletting aid than is the microbial cellulose produced in pellicle form by static cultivation processes.

A wide range of culture media are suitable for use in the process of the invention and the media can be formulated by the usual processes of experimentation familiar to those skilled in the art.

The invention is illustrated by the following examples:

EXAMPLE 1

| Medium | g.l$^{-1}$ |
| --- | --- |
| Peptone (oxoid) | 5 |
| Yeast extract (oxoid) | 5 |
| Na$_2$HPO$_4$ | 2.7 |
| Citric acid | 1.15 |
| Glucose | 20.0 |
| pH | 6.0 |

A flask containing 250 ml of this medium was incubated with 5 mls of the supernatant which resulted from the agitation of a 7 day old stationary culture of *Acetobacter aceti* subsp. orleanensis strain NCIB 8747, produced from colonies of cellulose producing cells picked out and separated from colonies of noncellulose producing cells after the cells generally had been plated out, and incubated in the same medium at 28° C. The flask was incubated at 120 rpm on a rotary shaker for 2 days at 28° C. After this time the resultant growth was transferred to a fermentation vessel containing 3 liters of the above medium except that the glucose concentration was 2.5 g.l$^{-1}$.

The fermenter was operated at 28° C., the agitation was at 500 rpm and the pH was maintained at pH 6 by addition of alkali. Supernatant glucose was monitored and when it dropped below 0.5–0.2 g.l$^{-1}$ glucose was added as a sterile solution at such a rate that the supernatant level was maintained at 0.5–0.2 g.l$^{-1}$.

After approximately 4 days the fermentation was ended and the yield of cellulose obtained was 5.2 g.l$^{-1}$.

EXAMPLE 2

The following basic medium was prepared:

| Yeast extract | 5.0 g/l |
| --- | --- |
| Peptone | 5.0 g/l |
| KH$_2$PO$_4$ | 1.9 g/l |
| NaH$_2$PO$_4$ | 1.56 g/l |
| (NH$_4$)$_2$SO$_4$ | 1.80 g/l |
| MgSO$_4$.7H$_2$O | 0.20 g/l |
| Citric Acid | 1.15 g/l |
| FeCl$_3$.6H$_2$O | 0.001 g/l |
| Trace Elements | 1.00 g/l |

The basic medium was thereafter used in 3 separate experiments using the following 3 microorganisms:
  Acetobacter sp strain NCIB 8623
  *Acetobacter pasteurianus* strain NCIB 7029
  *Acetobacter pasteurianus* strain NCIB 5346

The experimental procedure was the same with each microorganism. In each case 200 ml of the basic medium plus 20 g l$^{-1}$ glucose was sterilised in a 1000 ml baffled flask for 27 min at 121° C. Filter sterilised cellulase solution was added (2 mls of a 1/5 dilution of "CELLUCLAST" (RTM) sold by the Novo Company of Denmark).

A loopful of the microorganism to be tested in each experiment was removed from an agar plate and was used to inoculate the shake flask in each experiment. The flask was inoculated at 30° C. for 24 h at 200 rpm on an orbital shaker.

The culture produced above was used to produce microbial cellulose, the production conditions being the same in each experiment. In each case a fermenter with a marking volume of 3 to 4 liters was used, working under the following conditions:

| Temperature | 30° C. |
| --- | --- |
| pH | 5.00 (controlled using 2 M NaOH and 2M HCl) |
| Aeration | 0.25 V/V/M |
| Agitation | 500 rpm. |

The medium used was that described above, comprising the basic medium and glucose except that the initial concentration of glucose was 10 g l$^{-1}$. On exhaustion of the glucose, glucose was fed to the production fermenter at a rate of 1.0 g l$^{-1}$/h until the completion of the fermentation.

The results are set out in Table 1 and are shown in the graph of yield (g glucose/g cellulose) against time (h) in the drawing.

TABLE 1

| | Yield (gm cellulose/gm glucose) | | |
| --- | --- | --- | --- |
| Time (hrs) | NCIB 8623 | NCIB 7029 | NCIB 5346 |
| 16.5 | .010 | | .010 |
| 23 | | .095 | .042 |
| 28 | .070 | | |
| 41 | | | .070 |
| 45 | .040 | | |
| 48 | | .130 | .090 |
| 64 | .023 | .110 | .080 |

EXAMPLE 3

A shake flask was inoculated with strain NCIB 12584 (otherwise known as strain 99) which was grown for 24 hours after which time the purity of the resulting cellulose was assessed. This culture was then transferred to a fermenter containing a medium in which the carbon source glucose was present at a concentration of 10 g/l. The glucose concentration was monitored during growth of the culture and, when it was found to have fallen to 0.5 g/l, feeding of glucose to the fermenter was begun and was continued for 64 hours. Measurements of cell dry weight (g/l), cellulose dry weight (g/l) and glucose uptake (g/l) were taken at intervals and the results are set out in Table 2. This shows that the optimum yield of cellulose (i.e. g cellulose per g glucose) was achieved after 41 h. Thereafter glucose continued to be consumed to produce increased cell dry weight without producing further cellulose.

TABLE 2

| Fermentation time (h) | Dry cell wt. (g/l) | Cellulose dry wt. (g/l) | Glucose uptake (g/l) | Cellulose yield (g cell/ g gluc) |
| --- | --- | --- | --- | --- |
| 16.5 | 1.38 | 0.29 | 11.15 | 0.026 |
| 23.0 | 4.8 | 1.54 | 13.62 | 0.113 |
| 41.0 | 6.3 | 4.50 | 23.80 | 0.189 |
| 48 | 9.3 | 4.40 | 28.95 | 0.152 |
| 64.0 | 9.2 | 4.50 | 37.82 | 0.119 |

I claim:

1. A process for the production of extra-cellular microbial cellulose in which a bacterial strain capable of producing extra-cellular microbial cellulose is aerobically cultivated in a culture medium containing a carbon source wherein the process comprises the steps:
   (a) a growth step in which the bacterial strain is cultivated at a temperature within the range 15° C. to 35° C. and an initial pH within the range 4 to 6.5 in stirred batch culture until substantially all the carbon source present has been utilized and the culture is carbon limited;
   (b) an accumulation step carried out at a temperature within the range 15° C. to 35° C. and an initial pH within the range 4 to 6.5 in which the carbon source is supplied continuously to the carbon limited culture at a rate sufficient to maintain it in the supernatant at a level not greater than 0.5 g/l and to maintain the culture in carbon limitation thereby enabling microbial cellulose to accumulate during stirred cultivation;
   (c) a removal step in which bacterial cells and accumulated microbial cellulose are removed from the culture at the end of the accumulation step; and
   (d) a separation step in which microbial cellulose is separated from the cells.

2. A process according to claim 1 wherein the bacterial strain is an Acetobacter strain.

3. A process according to claim 2 wherein the bacterial strain is selected from the group consisting of Acetobacter strain NCIB 12584 and variants and mutants derived from this strain.

4. A process according to claim 1 wherein the initial carbon source concentration during growth step (a) is within the range 2 to 20 g/l.

5. A process according to claim 1 wherein during accumulation step (b) the carbon source is supplied to the culture at a concentration within the range 1 to 10 g/l per hour.

6. A process according to claim 1 wherein the carbon source is a carbon source for growth of the bacterial strain.

7. A process according to claim 1 wherein during separation step (d) the bacterial cell/cellulose mass is treated with a sodium hydroxide solution having a concentration in the range 0.1 to 5.0%.

* * * * *